United States Patent
Nakagawa et al.

(10) Patent No.: US 7,276,745 B2
(45) Date of Patent: Oct. 2, 2007

(54) GAS SENSOR

(75) Inventors: Shinichi Nakagawa, Kounan Aichi (JP); Yoshihiro Nakano, Komaki Aichi (JP); Masahito Kida, Nisikasugai Aichi (JP); Takio Kojima, Ichinomiya Aichi (JP)

(73) Assignee: NGK Spark Plug Co., Ltd., Aichi-ken (JP)

( * ) Notice: Subject to any disclaimer, the term of this patent is extended or adjusted under 35 U.S.C. 154(b) by 0 days.

(21) Appl. No.: 11/358,621

(22) Filed: Feb. 21, 2006

(65) Prior Publication Data

US 2006/0185420 A1 Aug. 24, 2006

(30) Foreign Application Priority Data

Feb. 22, 2005 (JP) ............................. 2005-046138
Dec. 15, 2005 (JP) ............................. 2005-361140

(51) Int. Cl.
*H01L 23/58* (2006.01)
*G01N 7/00* (2006.01)

(52) U.S. Cl. ..................................... 257/253; 73/31.06

(58) Field of Classification Search ............... 257/253; 73/31.06

See application file for complete search history.

(56) References Cited

U.S. PATENT DOCUMENTS

| | | | |
|---|---|---|---|
| 4,259,292 A | | 3/1981 | Ichinose et al. ............... 422/98 |
| 4,703,555 A | * | 11/1987 | Hubner ......................... 29/611 |
| 4,792,433 A | | 12/1988 | Katsura et al. ................ 422/98 |
| 5,250,170 A | | 10/1993 | Yagawara et al. ........... 204/431 |
| 5,821,402 A | * | 10/1998 | Okajima et al. ............. 73/23.2 |
| 5,849,165 A | * | 12/1998 | Kojima et al. ............... 204/429 |

(Continued)

FOREIGN PATENT DOCUMENTS

JP 4-127047 4/1992

(Continued)

OTHER PUBLICATIONS

European Search Report for European Patent Application No. 06 00 3613.4, Jun. 2, 2006.

(Continued)

*Primary Examiner*—Michael Cygan
(74) *Attorney, Agent, or Firm*—Kusner & Jaffe (57) ABSTRACT

The present invention provides a gas sensor having excellent humidity resistance even if used in a high temperature and high humidity atmosphere. According to the present invention, a gas sensor is comprised of: a silicon substrate; a metal-oxide semiconductor portion comprised mainly of $SnO_2$ and formed on the substrate; and a catalytic portion comprised of Pd and dispersed on a surface of the metal-oxide semiconductor portion, wherein the metal-oxide semiconductor portion and the catalytic portion constitute a gas sensing portion. Furthermore, an insulating portion comprised mainly of $SiO_2$ is formed dispersedly on a surface of the gas sensing portion. Further, the catalytic portion and the insulating portion are formed on the surface of the metal-oxide semiconductor portion so that the surface additive rate, which is expressed by Si/(Pd+Si) representing the ratio in the number of atoms of Si to Pd, of the gas sensing portion having the insulating portion may be 65% or more to 97% or less, and so that the surface additive rate, which is expressed by Si/(Sn+Si) representing the ratio in the number of atoms of Si to Sn, of the gas sensing portion may be 75% or more to 97% or less.

7 Claims, 3 Drawing Sheets

U.S. PATENT DOCUMENTS

| | | | |
|---|---|---|---|
| 5,942,676 A | 8/1999 | Potthast et al. | 73/31.06 |
| 6,325,979 B1 | 12/2001 | Hahn et al. | 422/88 |
| 6,550,310 B1 | 4/2003 | Liu et al. | 73/31.05 |

FOREIGN PATENT DOCUMENTS

| | | |
|---|---|---|
| JP | 5-005713 | 1/1993 |
| JP | 5-005715 | 1/1993 |
| JP | 5-322821 | 12/1993 |
| JP | 6-050919 | 2/1994 |
| JP | 11-183420 | 7/1999 |
| JP | 2001305089 | 10/2001 |
| JP | 2005-030907 | 2/2005 |

OTHER PUBLICATIONS

Japanese Office Action for Japanese Patent Application No. 2005-361140, Jul. 7, 2007, including English translation of relevant portions.

* cited by examiner

GAS SENSOR

FIELD OF INVENTION

The present invention relates to a gas sensor employing a metal-oxide semiconductor.

BACKGROUND OF THE INVENTION

Conventionally, it is known that a gas sensor employs a metal-oxide semiconductor, such as tin oxide ($SnO_2$) as a sensitive layer, and is capable of (a) detecting whether or not a gas to be detected is present, or (b) detecting a concentration variance thereof by means of a change in electrical characteristics (e.g., change in resistance) of the metal-oxide semiconductor. The metal-oxide semiconductor used in the gas sensor has a characteristic in which the number of conduction electrons in the metal-oxide semiconductor decreases and the resistance increases due to adsorption of the negative charge of oxygen ($O_2^-$) in the atmosphere on to the surface of the metal-oxide semiconductor. In such a state, if any reducing gas (such as carbon monoxide) is present as a gas to be detected in a measurement atmosphere, $O_2^-$ adsorbed on to the surface of the metal-oxide semiconductor will be desorbed, thus decreasing the resistance of the metal-oxide semiconductor. Based on such change in resistance of the metal-oxide semiconductor, the gas sensor may detect the gas to be detected. That is, the sensitivity of the gas sensor may be indicated by the resistance ratio of the metal-oxide semiconductor according to a presence or absence of the gas to be detected.

Since the metal-oxide semiconductor is susceptible to humidity, the sensitivity of the gas sensor tends to deteriorate under the influence of humidity. If the humidity increases in a measurement atmosphere, the quantity of moisture in the measurement atmosphere adsorbed as hydroxyl group $OH^-$ on to a site where $O_2^-$ should be adsorbed will increase. As a result, an adsorption quantity of $O_2^-$ on to the surface of the metal-oxide semiconductor will decrease. Therefore, the resistance of the metal-oxide semiconductor in the measurement atmosphere in which the gas to be detected is absent becomes small, when it should normally be high. Moreover, if the humidity in the measurement atmosphere is high, the amount of adsorption of hydroxyl group $OH^-$ will increase, thereby reducing the quantity of $O_2^-$ adsorbed. Furthermore, hydroxyl group $OH^-$ adsorbed on to the metal-oxide semiconductor is not desorbed by the gas to be detected. Even if the gas to be detected is present in the measurement atmosphere, the resistance of the metal-oxide semiconductor will not be small, but large. Thus, when the humidity in the measurement atmosphere increases, the sensitivity of the gas sensor deteriorates.

Therefore, by adding (1) a quinquevalent transition metal, such as vanadium, niobium and tantalum, and (2) a trivalent transition metal, such as chromium, to the metal-oxide semiconductor which serves as a gas detection body (sensitive layer), a binding force between $O_2^-$ and the surface of the metal-oxide semiconductor becomes larger than that of hydroxyl group $OH^-$ and the surface of the metal-oxide semiconductor. Consequently, the humidity resistance of the gas sensor may be improved. (e.g., see Japanese Patent Application Laid-open (kokai) No. 2001-305089 (hereinafter "the '089 patent document"))

Problems to be Solved by the Invention

In a gas sensor disclosed in the '089 patent document, only a seasonal dependence under a relatively low load is employed when evaluating the humidity resistance. Humidity resistance under high temperature and high humidity atmosphere (e.g., 60° C., 95% Relative Humidity(RH)), which is required for an in-vehicle gas sensor, is not taken into consideration.

The present invention has been conceived to solve the problems thus far described and has an object to provide a gas sensor having excellent humidity resistance, even if used in a high temperature and high humidity atmosphere.

SUMMARY OF THE INVENTION

To accomplish the above object, a gas sensor of an embodiment of the present invention comprises: a gas sensing portion formed by a metal-oxide semiconductor portion whose electrical characteristic varies according to a gas to be detected and a catalytic portion dispersed on a surface of the metal-oxide semiconductor portion (i.e., the material of the catalytic portion is dispersed on the surface of the metal-oxide semiconductor portion); and an insulating portion formed on a surface of the gas sensing portion so that a part of the gas sensing portion may be exposed (i.e., the material of the insulating portion is dispersed on the surface of the gas sensing portion so that the insulating portion does not form a compact layer); wherein the metal-oxide semiconductor portion is comprised mainly of $SnO_2$, the catalytic portion is comprised of a noble metal M and the insulating portion is comprised mainly of $SiO_2$, wherein a first surface additive rate or ratio, which is expressed by Si/(M+Si) representing the ratio in the number of atoms of Si to M, of the gas sensing portion having the insulating portion is determined to be 65% or more to 97% or less, and a second surface additive rate or ratio, which is expressed by Si/(Sn+Si) representing the ratio in the number of atoms of Si to Sn, of the gas sensing portion is determined to be 75% or more to 97% or less.

The first and second surface additive rates or ratios are measures for determining the level of compactness of the respective layers.

Moreover, in addition to the embodiment, the noble metal M is preferably Pd or Pt.

Furthermore, in addition to the embodiment, the metal-oxide semiconductor portion, the catalytic portion and the insulating portion preferably assume a form of a thin film, respectively.

Moreover, in addition to the embodiment, preferably, the gas sensor further comprises: a silicon substrate; and an insulating layer formed on the silicon substrate and in which a heating element for heating the metal-oxide semiconductor portion are buried therein, wherein the silicon substrate includes an open space formed at a position directly below the heating element, and wherein the metal-oxide semiconductor portion is formed on the insulating layer so as to be directly above the heating element.

Effects of the Invention

In a first aspect of the present invention, a catalytic portion (catalyst substance) is dispersedly formed on a surface of a metal-oxide semiconductor portion, and an insulating portion is dispersedly formed on the surface of the metal-oxide semiconductor portion where the catalytic portion is formed (i.e. on a gas sensing portion). The first surface additive rate, which is expressed by Si/(M+Si), of the metal-oxide semiconductor portion is determined to be 65% or more to 97% or less, and the second surface additive rate, which is expressed by Si/(Sn+Si), of the same is determined to be 75% or more to 97% or less. That is, the metal-oxide semiconductor portion and the catalytic portion which constitute the gas sensing portion are exposed to the surface of the insulating portion so that the negative charge of the oxygen ($O_2^-$) in the atmosphere may be adsorbed on to the surface of the metal-oxide semiconductor portion, thereby functioning as a gas sensor. Furthermore, $SiO_2$ constituting the insulating portion has a characteristic which traps hydroxyl group $OH^-$, preventing $OH^-$ from being adsorbed on to an $O_2^-$ adsorption site of the metal-oxide semiconductor portion in a high temperature and high humidity atmosphere. The gas sensor of the present invention may demonstrate excellent detection accuracy and humidity resistance because the catalytic portion and the insulating portion are formed on the surface of the metal-oxide semiconductor portion so that the surface additive rate thereof may be within the above-mentioned ranges.

When the first surface additive rate expressed by $Si/(M+Si)$ of the metal-oxide semiconductor portion is less than 65%, or when the second surface additive rate expressed by $Si/(Sn+Si)$ of the same is less than 75%, a proportion where the metal-oxide semiconductor portion and the catalytic portion are exposed in between the insulating portions will be large. As a result, the proportion of the insulating portion will be relatively small, causing hydroxyl group $OH^-$ to be unlikely to be trapped in a high temperature and high humidity atmosphere whereby the sensitivity of the gas sensor (proportion of resistance value in the metal-oxide semiconductor portion when a gas to be detected is present vs. absent) will deteriorate. On the other hand, when the first surface additive rate expressed by $Si/(M+Si)$ of the metal-oxide semiconductor portion is larger than 97%, or when the second surface additive rate expressed by $Si/(Sn+Si)$ of the same is larger than 97%, a proportion where the metal-oxide semiconductor portion and the catalytic portion are exposed in between the insulating portions will be small. That is, since the $O_2^-$ adsorption site of the gas sensor lessens, irrespective of the existence of the gas to be detected, the resistance of the metal-oxide semiconductor portion will hardly change (i.e. remain at a large value), resulting in a deterioration of the sensitivity of the gas sensor.

Moreover, since the insulating portion is comprised mainly of $SiO_2$, it may be inexpensively manufactured, as well as reducing environmental load.

In addition, in the present invention, the surface additive rate is obtained from the number of atoms measured by an X-ray photoelectron spectroscopy (XPS). In detail, a photoelectron peak area of an element subjected to a measurement among the elements existing on the metal-oxide semiconductor portion is measured by an X-ray surface analyzer (e.g., Quantera SXM, manufactured by Physical Electronics) on the condition that a detection depth is 4-5 nm (45 degrees of extraction angles) in the detection area of 100 μm, using an A1K α ray (1486 keV). Then, the number of atoms of each element, which is subjected to the measurement, is determined quantitatively (relative determinate quantity) by the equation shown in (1). The above-mentioned surface additive rate is calculated according to the number of atoms of thus-determined quantity of each element.

$$Ci = \{(Ai/RSFi)/(\Sigma iAi/RSFi)\} \times 100 \quad (1)$$

wherein, $Ci$ shall represent a determined quantity value (atomic%) of the element i subjected to the measurement, $Ai$ shall represent a photoelectron peak area of the element i subjected to the measurement, and $RSFi$ shall represent a relative sensitivity coefficient of the element i subjected to the measurement.

Moreover, in the present invention, "Main component" denotes a component that occupies 80% by weight or more, preferably 90% by weight or more, further preferably 95% by weight or more of the total components contained.

In a second aspect of the present invention based on the first aspect thereof, since a gas sensor uses Pd or Pt as a noble metal M which constitutes the catalytic portion, the gas sensor of the present invention demonstrates excellent durability regarding current application and excellent sensitivity to concentration change in a reducing gas in a measurement atmosphere.

In a third aspect of the present invention based on the second aspect thereof, the gas sensor may effectively protect the adsorption site of $O_2^-$ in the surface of the metal-oxide semiconductor portion by the insulating portion formed in a thin film, enabling the gas sensor to have an excellent humidity resistance, as well as an excellent durability regarding current application.

In a fourth aspect of the present invention, the metal-oxide semiconductor portion constituting the gas sensing portion is formed on an insulating layer so as to be directly above a heating element, and an open space portion is formed at a position directly below the heating element in the silicon substrate which is formed by laminating the insulating layer. Therefore, the metal-oxide semiconductor portion may be effectively heated by the heating element when the gas sensor is in use. By effectively heating the metal-oxide semiconductor portion using the heating element, the metal-oxide semiconductor portion will be well activated, resulting in a better detection of the concentration change in the gas to be detected in the measurement atmosphere.

Availability in the Industry

The present invention is applicable to a gas sensor for detecting a reducing gas.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF THE INVENTION

Best Mode for Carrying Out the Invention

Hereafter, an embodiment of a gas sensor 1 materializing the present invention will be described below with reference to the drawings.

Figure 1:
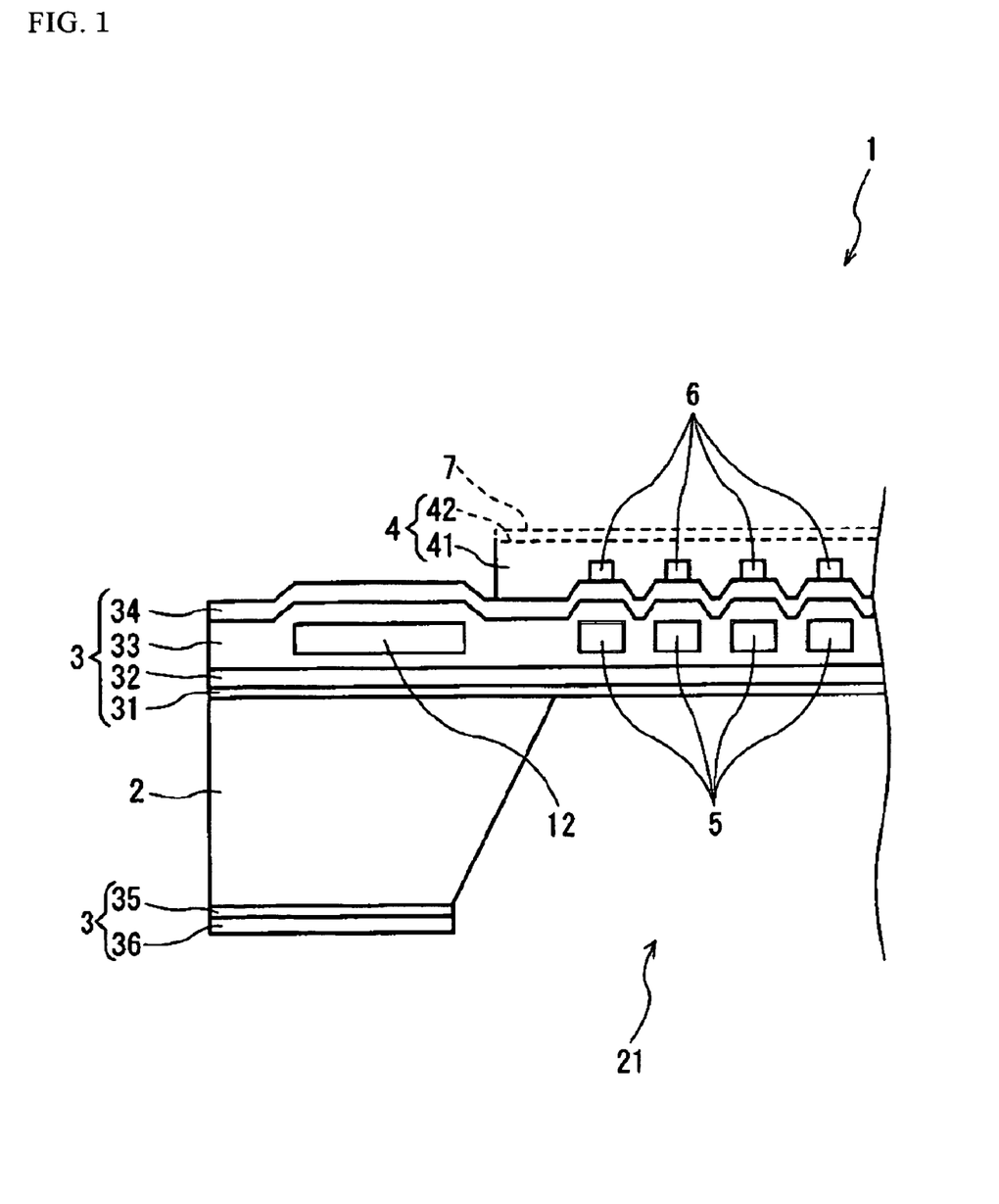
FIG. 1 is a local sectional view of a gas sensor 1 (in detail, the view cross sectioned from left hand side to right hand side of the document, including a position which contains a gas sensing portion 4 in a gas sensor 1 shown in FIG. 3)
Figure 2:
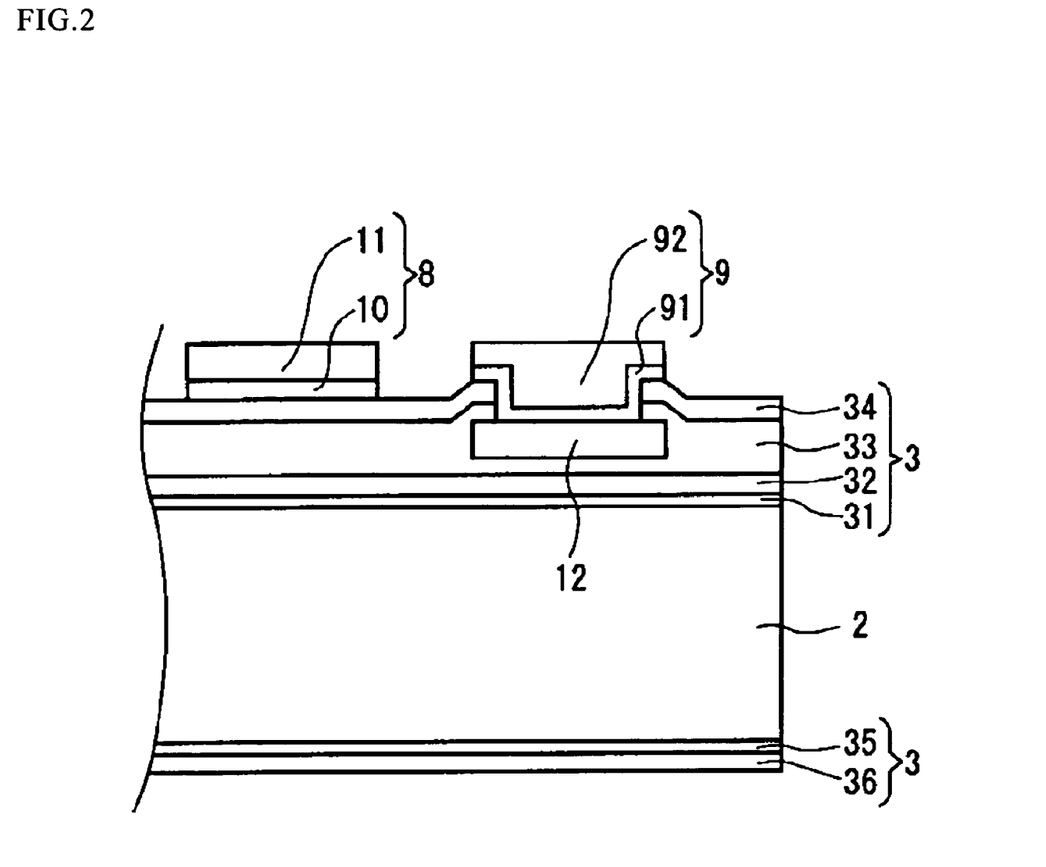
FIG. 2 is a local sectional view showing a vicinity of a contact for heating element 9 of the gas sensor 1.
Figure 3:
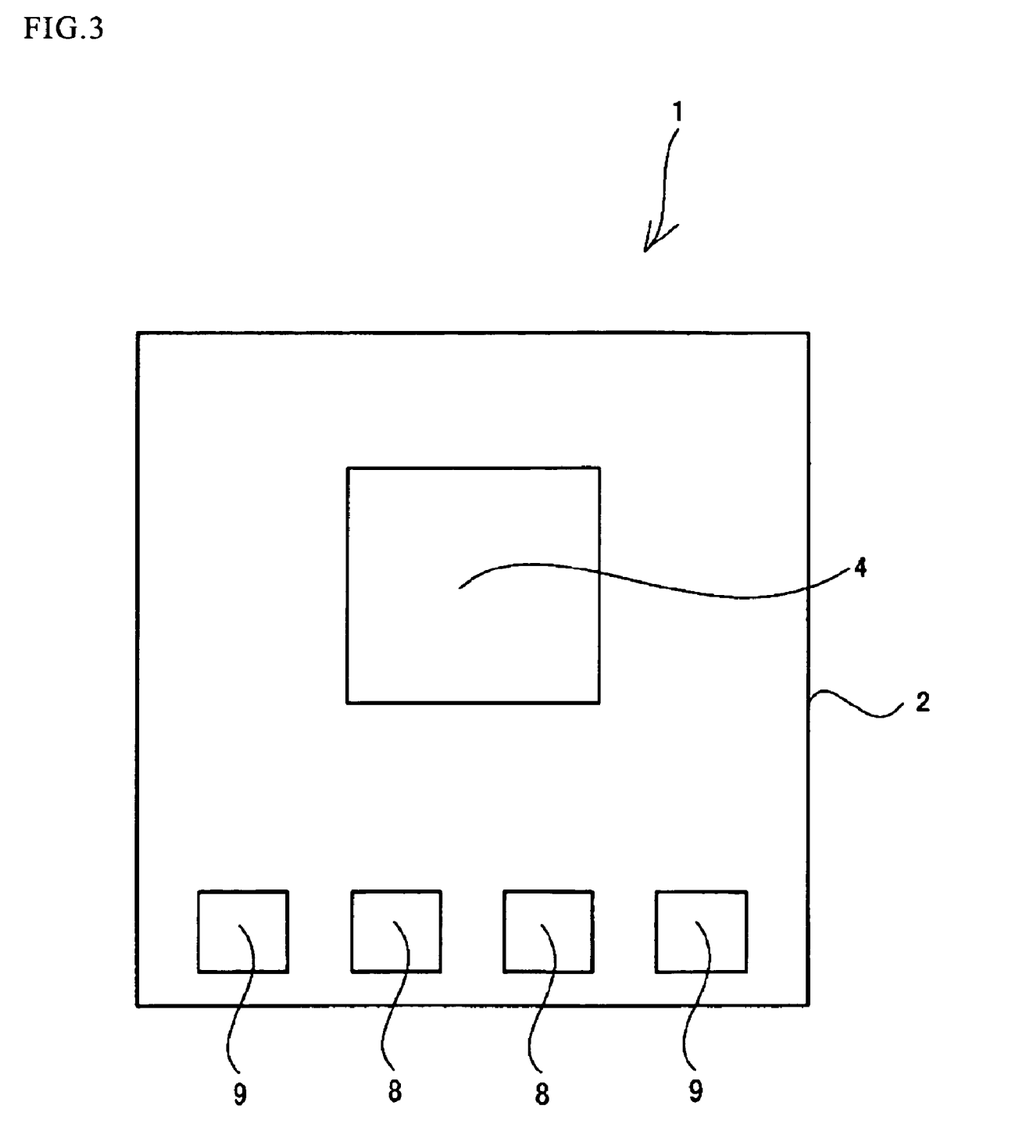
FIG. 3 is a top plan view viewing from a side where a gas-sensing portion 4 of the gas sensor 1 is formed.

First, the structure of the gas sensor 1 will be explained with reference to FIG. 1 and FIG. 2. FIG. 1 is a local sectional view of the gas sensor 1. FIG. 2 is a local sectional view showing a vicinity of a contact for heating element 9 of the gas sensor 1. FIG. 3 is a top plan view viewing from a side where a gas-sensing portion 4 of the gas sensor 1 is formed.

As shown in FIG. 3, the gas sensor 1 assumes a rectangular form in a top plan view and has insulating portions 3 formed on both top and bottom surfaces of a silicon substrate 2, in which the insulating portion 3 formed on one of the surfaces has a gas sensing portion 4 and an insulating portion 7. The gas sensor 1 is capable of detecting a variation of gas concentration to be detected by utilizing its electrical characteristic which changes according to a gas to be detected. Here, the gas to be detected is a reducing gas which includes, for example, carbon monoxide gas, hydrocarbon-system gases (LPG, city gas, natural gas, methane, halogenation hydrocarbon system gas, etc.), alcoholic-system gas, aldehyde-system gas, hydrogen gas, hydrogen sulfide gas. Specifically, the gas sensor 1 is suitable for detecting a variation of carbon monoxide gas concentration.

The insulating portions 3 are constituted by insulating layers 31, 32, 33, 34 formed on one face of the silicon substrate 2, and insulating layers 35, 36 formed on the other face thereof. The insulating layers 31, 35 made of silicon oxide ($SiO_2$) are formed on both surfaces of the silicon substrate 2 in the thickness direction, respectively, so as to sandwich the silicon substrate 2. Further, the insulating layers 32, 36 made of silicon nitride ($Si_3N_4$) are formed on each outer surface of the insulating layers 31, 35, respectively. Moreover, the insulating layer 33 made of silicon oxide is formed on the outer surface of the insulating layer 32, and the insulating layer 34 made of silicon nitride is laid over the insulating layer 33.

In the insulating layer 33, a heating element 5 used for heat cleaning are buried therein, which heats the metal-oxide semiconductor portion so as to return the gas sensor 1 to its initial state when the sensitivity (proportion of resistance value in a metal-oxide semiconductor portion when a gas to be detected is present or absent) of the gas sensor 1 falls. Also a lead portion 12 electrically connected to the heating element 5 is buried in the insulating layer 33, and as shown in FIG. 2, a contact 9 for heating element 5 connected to an external circuit is formed at an end of the lead portion 12. The heating element 5 and the lead portion 12 are made to have a two-layered structure comprised of a platinum (Pt) layer and a tantalum (Ta) layer. Moreover, the contact 9 for heating element 5 has a structure where a contact pad 92 made of gold (Au) is formed on the surface of an extraction electrode 91 comprised of a titanium layer (Ti) and a platinum layer. In addition, the contacts 9 for heating element 5 are formed in pairs in the gas sensor 1 (see FIG. 3).

Moreover, as shown in FIG. 1, an open space portion 21 is formed at a face of the silicon substrate 2 where the insulating layer 36 is formed. The open space portion 21 is formed in such a manner that a part of silicon substrate 2 and a part of insulating layers 35, 36 are removed so that a part of insulating layer 31 is exposed. The open space portion 21 is located at a position corresponding to the heating element 5 which are buried in the insulating layer 33 (i.e., directly below the heating elements 5).

Next, as shown in FIG. 1, on the surface of the insulating layer 34, electrodes 6 located on the heating element 5 and a lead portion 10 (refer to FIG. 2) for electrically connecting to the electrode 6 is formed. Similar to the extraction electrode 91 of the contact 9 for heating element 5, the electrodes 6 and the lead portion 10 are comprised of a titanium layer formed on the insulating layer 34 and a platinum layer laid over the titanium layer. Moreover, as shown in FIG. 2, a contact pad 11 made of gold is formed over an end of the lead portion 10 as a metal-oxide semiconductor contact portion 8 for providing a contact to an external circuit. In addition, the metal-oxide semiconductor contact portion 8 is formed in pairs in the gas sensor 1.

Next, as shown in FIG. 1, a gas sensing portion 4 is formed on the insulating layer 34 so as to cover the electrodes 6, and is comprised of a metal-oxide semiconductor portion 41 comprised mainly of tin oxide ($SnO_2$) and a catalytic portion 42 comprised of palladium (Pd) and dispersely formed on the surface of the metal-oxide semiconductor portion 41. That is, the palladium particles of the catalytic portion 42 of the present embodiment are dispersed on the surface of the metal-oxide semiconductor portion 41. Moreover, an insulating portion 7 made of silicon oxide ($SiO_2$) is dispersedly formed on the surface of the gas sensing portion 4. In addition, the metal-oxide semiconductor portion 41 (gas sensing portion 4) is formed on the insulating portion 3 (in detail, on the insulating layers 33, 34) so as to be directly above the heating element 5.

Incidentally, in the gas sensor 1 of the present embodiment, the catalytic portion 42 of the gas sensing portion 4 and the insulating portion 7 are formed on the surface of the metal-oxide semiconductor portion 41 in the order mentioned with the composition thereof dispersed, respectively. This means that neither the surface of the metal-oxide semiconductor portion 41 is entirely covered by the catalytic portion 42, nor are the surfaces of the metal-oxide semiconductor portion 41 and the catalytic portion 42 entirely covered by the insulating portion 7. This was proved by a result of a measurement using XPS where Si, Pd and Sn were observed on the surface of the gas sensing portion 4 having the insulating portion 7 of the gas sensor 1. Notably, the analysis (measurement) by XPS in the present embodiment was performed using the above-described apparatus under the same condition as the aforementioned condition. In the present embodiment, based on a result of the evaluation mentioned later, the first surface additive rate, which is expressed by Si/(Pd+Si) representing the number ratio of atoms of Si (constituting the insulating portion 7 on the surface thereof) and Pd (constituting the catalytic portion 42), is determined to be 65% or more to 97% or less, and the second surface additive rate, which is expressed by Si/(Sn+Si) representing the number ratio of atoms of Si and Sn (constituting the metal-oxide semiconductor portion 41), is determined to be 75% or more to 97% or less.

FIRST EMBODIMENT

In order to confirm the effect of the present invention regarding the gas sensor 1 described above, seven samples each having different surface additive rate (of Si in the metal-oxide semiconductor portion 41, a noble metal M constituting the catalytic portion 42 and Sn) were produced based on each process explained below, and then they were subjected to an evaluation. In addition, an unfinished article of the gas sensor 1 in the production process will be called a substrate.

(1) Rinsing of Silicon Substrate 2

First, a silicon substrate 2 having a thickness of 400 μm was immersed in a rinsing liquid and subjected to a rinsing treatment.

(2) Formation of Insulating Layers 31, 35

The silicon substrate 2 was put into a heat treatment furnace and subjected to a thermal-oxidization treatment to form a silicon oxide layer (insulating layers 31 and 35) having a thickness of 100 nm all over the silicon substrate 2.

(3) Formation of Insulating Layers 32, 36

Next, by a LP-CVD using $SiH_2Cl_2$ and $NH_3$ as a source gas, a silicon-nitride layer (insulating layer 32) having a thickness of 200 nm was formed on one face of the silicon substrate 2. Similarly, a silicon-nitride layer (insulating layer 36) having a thickness of 100 nm was formed on the other face of the silicon substrate 2.

(4) Formation of a part of Insulating layer 33 (Lower Layer)

Next, by a plasma CVD using TEOS and $O_2$ as a source gas, a silicon oxide layer (a part of insulating layer 33) having a thickness of 100 nm was formed on the surface of the insulating layer 32.

(5) Formation of Heating Element 5 and Lead Portion 12

Then, using a DC sputtering apparatus, a tantalum layer having a thickness of 20 nm was formed on the surface of the insulating layer 33, and a platinum layer having a thickness of 220 nm was formed over the tantalum layer. After the sputtering treatment, a resist was patterned by a photolithography, and the patterns of heating element 5 and the lead portion 12 were formed by wet-etching treatment.

(6) Formation of Insulating Layer 33 (Upper Layer)

Similar to (4), by the plasma CVD using TEOS and $O_2$ as a source gas, a silicon oxide layer (insulating layer 33 (upper layer)) having a thickness of 100 nm was formed on the surfaces of the insulating layer 33 (lower layer) and the heating element 5. Thus, the heating element 5 and the lead portion 12 were buried in the insulating layer 33 having a thickness of 200 nm.

(7) Formation of Insulating Layer 34

Furthermore, similar to (3), by the LP-CVD using $SiH_2Cl_2$ and $NH_3$ as a source gas, a silicon-nitride layer (insulating layer 34) having a thickness of 200 nm was formed on the surface of the insulating layer 33.

(8) Formation of Openings for Contacts for Heating Element 9

Subsequently, the resist was patterned by the photolithography. Then, the insulating layers 33 and 34 were etched by a dry etching method to form a hole in the portion where a contact 9 for heating elements 5 would be formed so that a part of an end of the lead portion 12 could be exposed.

(9) Formation of Electrodes 6, Lead Portions 10 and Extraction Electrodes 91

Next, using the DC sputtering apparatus, a tantalum layer having a thickness of 20 nm was formed on the surface of the insulating layer 34, and a platinum layer having a thickness of 40 nm was formed over the tantalum layer. After the sputtering treatment, the resist was patterned by the photolithography, and the patterns of electrodes 6, lead portions 10 and extraction electrodes 91 were formed by wet-etching treatment.

(10) Formation of Contact Pads 11, 92

Then, a gold layer having a thickness of 400 nm was formed using the DC sputtering apparatus on the surface of the substrate where the electrodes were formed. After the sputtering treatment, the resist was patterned by the photolithography, and the contact pads 11, 92 were formed by wet-etching treatment.

(11) Formation of Open Space Portion 21

Subsequently, the resist was patterned by the photolithography, and an insulating film used as a mask was formed by dry etching treatment. Then, the silicon substrate 2 was immersed in a TMAH solution and subjected to an anisotropic etching to open the face where the insulating layers 35, 36 were formed and to form an open space portion 21 at a position corresponding to the heating element 5 so as to expose the insulating layer 31.

(12) Formation of Gas Sensing Portion 4 and Insulating Portion 7

Next, a gas sensing portion 4 was formed by the following method on the surface of the insulating layer 34. First, the tin oxide layer (a metal-oxide semiconductor portion 41) was formed at the position corresponding to the heating element 5 and the open space portion 21 using a RF sputtering apparatus. Subsequently, a catalytic portion 42 was formed on the surface of the tin oxide layer by providing a noble metal M (in detail, Pd or Pt) thereon using the RF sputtering apparatus to complete the gas sensing portion 4. Furthermore, the silicon oxide was adhered to the surface of the gas sensing portion 4 using the RF sputtering apparatus to complete an insulating portion 7. In each process mentioned above, the substrate was heated so that the temperature of each portion was in the range of 50-400° C. when formed into a thin film. The metal-oxide semiconductor portion 41, the catalytic portion 42 and the insulating portion 7 are formed in the order mentioned according to the above-described process. The catalytic portion 42 and the insulating portion 7 were formed by adjusting a sputtering treatment period so that the first surface additive rate expressed by Si/(M+Si) could become 65% or more to 97% or less, and the second surface additive rate expressed by Si/(Sn+Si) could become 75% or more to 97% or less. These rates were obtained by measuring the surface of the insulating portion 7 using XPS.

(13) Heat Treatment of Substrate

The substrate was inserted in the heat treatment furnace and subjected to heat treatment for 1-10 hours at 300-500° C. in the atmosphere.

(14) Cutting of Substrate and Aging Treatment of Gas Sensor

The substrate was cut using a dicing saw to obtain a gas sensor 1 having the size of 2.6 mm×2 mm as viewed from above. Then the gas sensor 1 is subjected to an aging treatment for over 100 hours at 250° C. in the atmosphere to complete the gas sensor 1.

In addition, thus-produced gas sensor 1 will be mounted on a circuit board having a sensor control circuit etc.

The evaluation on the sensitivity to the gas to be detected was performed to samples of the gas sensor 1 with Samples 1 to 6 using Pd as a noble metal M, which constituted the catalytic portion 42, and Sample 7 using Pt as a noble metal M. As shown in Table 1, the catalytic portion 42 of Samples 1 to 7 were formed so that the first surface additive rate of the metal-oxide semiconductor portion 41 expressed by Si/(M+Si) became 0, 67, 89, 97, 99, 33 and 96 (%), respectively. Furthermore, the insulating portion 7 of Samples 1 to 7 were formed so that the second surface additive rate of the metal-oxide semiconductor portion 41 expressed by Si/(Sn+Si) became 0, 76, 92, 97, 99, 77 and 97 (%), respectively.

Each sample was electrically connected to a measuring tool using a gold wire. Then each sample was placed in a relative humidity of 95% RH atmosphere at 60° C. and the heating element 5 was electrically connected and held for 50 hours so that the temperature thereof could be at 250° C. to perform a humidity resistance test. Moreover, while performing the test, a gas detection voltage was also applied to the metal-oxide semiconductor portion 41.

In the evaluation, the change in sensitivity to carbon monoxide (CO) gas before and after the humidity resistance test was compared. Here, the sensitivity to the CO gas was calculated on the basis of the resistance of the gas sensor measured by the following method. First, the resistance (Rair) of the gas sensor was measured using a base gas having a temperature of 25° C., a composition here where the base gas was a mixed gas with a composition of oxygen ($O_2$) (20.9 vol %) and nitrogen ($N_2$) (the remainder), and a relative humidity of 40% RH. Next, a surrounding atmosphere of the gas sensor was made into the atmosphere which CO gas of 30 ppm was mixed with the base gas in order to measure the resistance (Rgas) of the gas sensor at 5 seconds after mixing. Then, the ratio (Rgas/Rair) of both resistances was calculated as sensitivity (gas sensitivity response value). In addition, the value of sensitivity enabling the detection of the gas to be detected is less than 0.95.

Sample 1 had the sensitivity of 0.80 measured before the humidity resistance test and 0.98 after the test. Then, current was applied to the heating element to subject the sensor to heat cleaning for 30 seconds at 350° C., and subsequently the sensitivity was measured again. The result was 0.97, indicating no recovery. Then, the heating element of Sample 1 was used again to subject the sensor to heat cleaning for 1 minute at 500° C. The sensitivity of the gas sensor became 0.90. Sample 6 had the sensitivity of 0.94 measured before humidity resistance test and 0.97 after the test.

The sensitivity of Samples 2 to 4 before the humidity resistance test was 0.80, 0.76 and 0.81, respectively, and following the test was 0.92, 0.90 and 0.93, respectively. Similar to the above, the samples were subjected to the heat cleaning for 30 seconds at 350° C. As a result, the sensitivity of Samples 2 to 4 became 0.84, 0.80 and 0.88, respectively.

Sample 5 indicated the sensitivity of 0.97 before the humidity resistance test.

On the other hand, Sample 7 using Pt as a noble metal M had the sensitivity of 0.85 before the humidity resistance test and 0.89 after the test. Similar to the above, Sample 7 was subjected to the heat cleaning for 30 seconds at 350° C. The sensitivity of Sample 7 became 0.86.

Sample 6 had a first surface additive rate of less than 65%, expressed by Si/(M+Si). Also Pd used as a noble metal M in the catalytic portion 42 was excessively exposed in between the insulating portions 7, limiting the formation of the insulating portion 7 to a relatively low amount. As a result, deterioration of the sensitivity of Sample 6 was observed after the humidity resistance test.

Samples 2 to 4 had the first surface additive rates expressed by Si/(M+Si) of 65% or more to 97% or less, and had the second surface additive rates expressed by Si/(Sn+Si) of 75% or more to 97% or less. The sensitivity of Samples 2 to 4 before and after the test indicated less than 0.95—the value of sensitivity enabling to detect the gas to be detected. Furthermore, it was confirmed that the sensitivity was recovered to the value near the value before the test if the low temperature heat cleaning at 350° C. was performed after the test.

Moreover, in Sample 7 which employed Pt as a noble metal M in the catalytic portion 42, if the first surface additive rate expressed by Si/(M+Si) was 65% or more to 97% or less, and the second surface additive rate expressed by Si/(Sn+Si) was 75% or more to 97% or less, a good sensitivity of the gas sensor similar to those in Samples 2 to 4 was observed.

In addition, the invention is not particularly limited to the embodiments described above but may be changed or modified in various ways within the scope of the invention. For example, although the silicon substrate 2 was made of silicone, it may also be produced from alumina or other semiconductor material. Moreover, a planer shape of the gas sensor 1 does not necessarily assume a form of a rectangle, but a polygon or a circular and the size and thickness thereof are not limited. Furthermore, the metal-oxide semiconductor portion 41, the catalytic portion 42 and the insulating portion

TABLE 1

| | | | | Response Rate of Gas Sensitivity | | | |
|---|---|---|---|---|---|---|---|
| Sample | Element of Noble Metal M | Surface additive rate (%) Si/(M + Si) | Surface additive rate (%) Si/(Sn + Si) | Before humidity resistance test | After humidity resistance test | After heat cleaning (350° C. × 30 sec) | After heat cleaning (500° C. × 1 min) |
| 1 | Pd | 0 | 0 | 0.80 | 0.98 | 0.97 | 0.90 |
| 2 | Pd | 67 | 76 | 0.80 | 0.92 | 0.84 | — |
| 3 | Pd | 89 | 92 | 0.76 | 0.90 | 0.80 | — |
| 4 | Pd | 97 | 97 | 0.81 | 0.93 | 0.88 | — |
| 5 | Pd | 99 | 99 | 0.97 | — | — | — |
| 6 | Pd | 33 | 77 | 0.94 | 0.97 | — | — |
| 7 | Pt | 96 | 97 | 0.85 | 0.89 | 0.86 | — |

As a result of the evaluation, deterioration of the sensitivity due to adsorption of hydroxyl group $OH^-$ on to the metal-oxide semiconductor portion 41 after the test was observed in Sample 1 where no insulating portion 7 comprised mainly of $SiO_2$ was formed. Any recovery of the sensitivity in Sample 1 was not observed after the low temperature heat cleaning at 350° C. However, after the high temperature heat cleaning at 500° C., which imposed a large load on the metal-oxide semiconductor portion 41, recovery of the sensitivity in Sample 1 was confirmed.

Moreover, Sample 5, which had the surface additive rate of 99% in both Si/(M+Si) and Si/(Sn+Si), the sensitivity thereof was not good even in the normal condition (i.e., before the humidity resistance test) because $SnO_2$, which constitutes the metal-oxide semiconductor portion 41, was hardly exposed in between the insulating portions 7.

7 in the above-described embodiment were formed in a thin film using the sputtering method. However, a vapor phase epitaxy method (e.g. vapor deposition) other than the sputtering method may be used.

DESCRIPTION OF REFERENCE NUMERALS 1 gas sensor
2 silicon substrate
3 insulating layer(s)
4 gas sensing portion
5 heating element
6 electrodes
7 insulating portion
8 metal-oxide semiconductor portion
9 contact 10 lead portion
11 contact pad
12 lead portion21 open space portion
31 $SiO_2$ layer
32 $Si_3N_4$ layer
33 $SiO_2$ layer
34 $Si_3N_4$ layer
35 $SiO_2$ layer
36 $Si_3N_4$ layer
41 metal-oxide semiconductor portion
42 catalytic portion
91 extraction electrode
92 contact pad Having described the invention, the following is claimed:

1. A gas sensor comprising:
    a gas sensing portion formed by a metal-oxide semiconductor portion whose electrical characteristic varies according to a gas to be detected and a catalytic portion dispersed on a surface of the metal-oxide semiconductor portion; and
    an insulating portion formed on a surface of the gas sensing portion so that a part of the gas sensing portion may be exposed;
    wherein the metal-oxide semiconductor portion is comprised mainly of $SnO_2$, the catalytic portion is comprised of a noble metal M and the insulating portion is comprised mainly of $SiO_2$,
    wherein a first surface additive rate, which is expressed by Si/(M+Si) representing the ratio in the number of atoms of Si to M, of the gas sensing portion having the insulating portion is determined to be 65% or more to 97% or less, and a second surface additive rate, which is expressed by Si/(Sn+Si) representing the ratio in the number of atoms of Si to Sn, of the gas sensing portion is determined to be 75% or more to 97% or less, wherein said first surface additive rate and said second surface additive rate is obtained by the number of atoms measured by X-ray photoelectron spectroscopy (XPS) at a detection depth in the range of 4-5 nm at a 45 degree extraction angle in a detection area of 100 µm.

2. A gas sensor as claimed in claim 1, wherein the noble metal M is Pd or Pt.

3. A gas sensor as claimed in claim 1,
    wherein the metal-oxide semiconductor portion, the catalytic portion and the insulating portion assume a form of a thin film, respectively.

4. A gas sensor as claimed in claim 2,
    wherein the metal-oxide semiconductor portion, the catalytic portion and the insulating portion assume a form of a thin film, respectively.

5. A gas sensor as claimed in claim 1, further comprises:
    a silicon substrate; and
    an insulating layer formed on the silicon substrate and in which a heating element for heating the metal-oxide semiconductor portion is buried therein,
    wherein the silicon substrate includes an open space formed at a position directly below the heating element, and
    wherein the metal-oxide semiconductor portion is formed on the insulating layer so as to be directly above the heating element.

6. A gas sensor as claimed in claim 2, further comprises:
    a silicon substrate; and
    an insulating layer formed on the silicon substrate and in which a heating element for heating the metal-oxide semiconductor portion is buried therein,
    wherein the silicon substrate includes an open space formed at a position directly below the heating element, and
    wherein the metal-oxide semiconductor portion is formed on the insulating layer so as to be directly above the heating element.

7. A gas sensor as claimed in claim 3, further comprises:
    a silicon substrate; and
    an insulating layer formed on the silicon substrate and in which a heating element for heating the metal-oxide semiconductor portion is buried therein,
    wherein the silicon substrate includes an open space formed at a position directly below the heating element, and
    wherein the metal-oxide semiconductor portion is formed on the insulating layer so as to be directly above the heating element.

* * * * *